(12) United States Patent
     Palumbo

(10) Patent No.: US 10,384,152 B2
(45) Date of Patent:     Aug. 20, 2019

(54) BACKSCATTER REDUCTANT ANAMORPHIC BEAM SAMPLER

(71) Applicants: TINTOMETER, GMBH, Dortmund (DE); Perry Palumbo, Fort Collins, CO (US)

(72) Inventor: Perry Palumbo, Fort Collins, CO (US)

( * ) Notice: Subject to any disclaimer, the term of this patent is extended or adjusted under 35 U.S.C. 154(b) by 242 days.

(21) Appl. No.: 15/511,107

(22) PCT Filed: Jun. 7, 2016

(86) PCT No.: PCT/US2016/036202
     § 371 (c)(1),
     (2) Date: Mar. 14, 2017

(87) PCT Pub. No.: WO2016/200802
     PCT Pub. Date: Dec. 15, 2016

(65) Prior Publication Data
     US 2017/0248795 A1     Aug. 31, 2017

Related U.S. Application Data

(60) Provisional application No. 62/315,298, filed on Mar. 30, 2016, provisional application No. 62/173,101, (Continued)

(51) Int. Cl.
     *H01J 40/14*     (2006.01)
     *B01D 19/00*     (2006.01)
     *G02B 5/04*     (2006.01)
     (Continued)

(52) U.S. Cl.
     CPC ........ *B01D 19/0042* (2013.01); *G01J 1/0477* (2013.01); *G01J 1/4257* (2013.01);
     (Continued)

(58) Field of Classification Search
     CPC .. B01D 19/0042; G01J 1/0477; G01J 1/4257; G02B 5/04; G02B 27/108; G02B 6/32; G02B 13/08; G02B 13/10; G02B 5/005
     (Continued)

(56) References Cited

U.S. PATENT DOCUMENTS 4,334,300 A * 6/1982 Arquie ................... G02B 27/09
                                                        359/732
5,396,325 A    3/1995 Carome et al.
(Continued)

FOREIGN PATENT DOCUMENTS

GB           2413858       11/2005

*Primary Examiner* — Georgia Y Epps
(74) *Attorney, Agent, or Firm* — Leyendecker & Lemire, LLC

(57) ABSTRACT

Embodiments of the present invention include a backscatter reductant anamorphic beam sampler. The beam sampler can be implemented to measure a power of a reference beam generated by an electromagnetic radiation source in proportion to a power of a working beam. The beam sampler can provide astigmatic correction to a divergence of the working beam along one axis orthogonal to a direction of propagation. The beam sampler can further be implemented to prevent backscatter from impinging upon a photodetector of the beam sampler resulting in a reduction of error and instability in measurements taken by the beam sampler.

20 Claims, 5 Drawing Sheets

Related U.S. Application Data filed on Jun. 9, 2015, provisional application No. 62/244,004, filed on Oct. 20, 2015, provisional application No. 62/174,243, filed on Jun. 11, 2015.

(51) Int. Cl.
| | |
|---|---|
| *G01J 1/04* | (2006.01) |
| *G01J 1/42* | (2006.01) |
| *G02B 5/00* | (2006.01) |
| *G02B 27/10* | (2006.01) |
| *G01N 21/53* | (2006.01) |
| *G01N 15/06* | (2006.01) |
| *G01N 21/05* | (2006.01) |

(52) U.S. Cl.
CPC ............ *G01N 21/53* (2013.01); *G02B 5/005* (2013.01); *G02B 5/04* (2013.01); *G02B 27/108* (2013.01); *G01N 15/06* (2013.01); *G01N 21/534* (2013.01); *G01N 2021/054* (2013.01)

(58) Field of Classification Search
USPC ...................................................... 250/578.1
See application file for complete search history.

(56) References Cited

U.S. PATENT DOCUMENTS

| | | | |
|---|---|---|---|
| 6,034,797 A * | 3/2000 | Ju ............................ | G02B 5/04 359/15 |
| 6,036,324 A | 3/2000 | Bernacki et al. | |
| 8,454,512 B2 | 6/2013 | Wang et al. | |
| 2008/0192350 A1* | 8/2008 | Yamada .................. | C03C 17/23 359/582 |
| 2012/0206735 A1* | 8/2012 | Rutten ...................... | G01J 1/04 356/622 |
| 2015/0055222 A1* | 2/2015 | Tamada ................. | G02B 1/115 359/581 |

\* cited by examiner

BACKSCATTER REDUCTANT ANAMORPHIC BEAM SAMPLER

CROSS-REFERENCE TO RELATED APPLICATION

This application claims the benefit of U.S. Provisional Application No. 62/173,101, filed Jun. 9, 2015, U.S. Provisional Application No. 62/244,004, filed Oct. 20, 2015, and U.S. Provisional Application No. 62/174,243, filed Jun. 11, 2015, and U.S. Provisional Application No. 62/315,298, filed Mar. 30, 2016.

FIELD OF THE INVENTION

Optics applicable to optical power measurement, electromagnetic beam measurement, and power control thereof.

BACKGROUND

Optical beam samplers are useful in a variety of applications where an energy of a beam of electromagnetic radiation needs to be determined. Typically, the energy needs to be determined for the purpose of control, compensation, and/or correction of variations in a power of a working beam without resulting in a significant reduction in the power of the working beam. Furthermore, a common requirement is to shape and homogenize the working beam of an optical system. The working beam is used for illumination of a specimen (or sample), for excitation of the specimen, and/or transmission through the specimen without preference to the rotational orientation of the working beam. The working beam is typically used without a need of further conditioning to remove variations in a cross-section intensity of the working beam.

Currently, a problem exists in using beam samplers of prior art where backscatter radiation, a result of an interaction of the working beam beyond the beam sampler, is reentrant to an output of the beam sampler and impinges upon a measuring means of the beam sampler. Due to single and/or multiple internal reflections within the beam sampler, backscatter is detected by the measuring means of the beam sampler, resulting in a sampling error of the working beam being greater than expected. To further detriment, measurement noise may be introduced into a measurement by interaction of the working beam with an object, such as a liquid surface, where instability in the liquid surface, due to vibration, movement, flow, etc., scatters energy inconsistently in direction and intensity. Instability in the backscattering surface is observed as measurement noise by the measuring means of the beam sampler. The problem is exasperated as additional optical surfaces are introduced into the optical system. For example, separate optics for field control of a radiation source, additional optics for shaping of the beam, and/or additional optics to correct astigmatism inherent in the radiating source. Based on currently available beam samplers, a removal of backscatter energy from impinging upon the measurement means is difficult and current beam samplers are prone to error in an assay of energy within the working beam.

DETAILED DESCRIPTION

Figure 1:
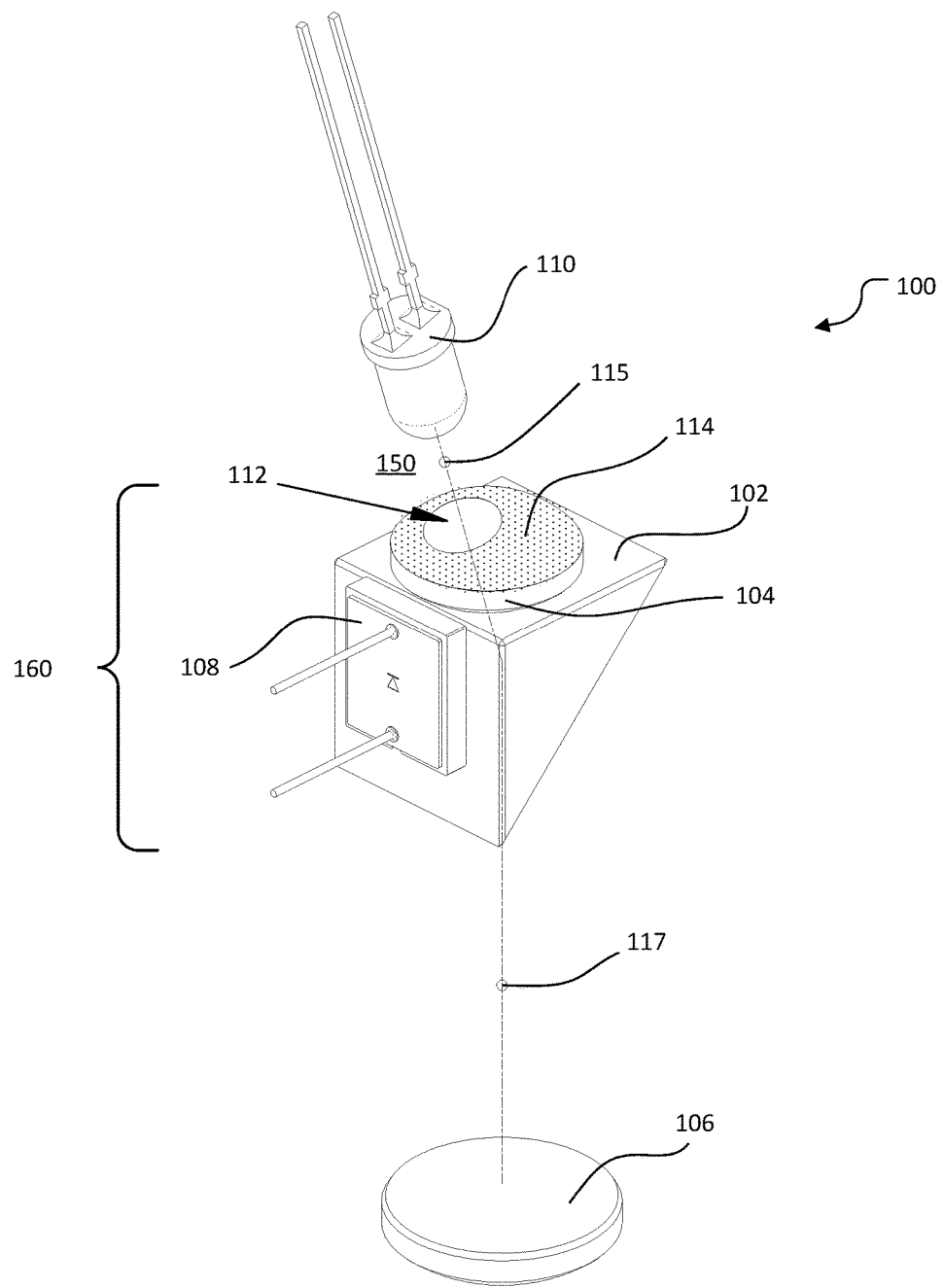
FIG. 1 is an isometric view of a backscatter reductant anamorphic beam sampler according to one embodiment of the present invention.

Embodiments of the present invention include a backscatter reductant anamorphic (BRA) beam sampler having an absorptive coating on a convex lens of the beam sampler. The BRA beam sampler can be implemented to reduce a measurement error of a beam sampler due to backscatter from a working beam impinging upon an object or surface, which reflects or partially reflects the working beam into the output of the beam sampler. At least some embodiments of the present invention can be implemented to remove intensity variations within a cross-section of a working beam at a select distance from the beam sampler without significant loss of energy.

In one embodiment, the BRA beam sampler can be implemented to (i) shape radiation emitted from an electromagnetic radiation source having orthogonal fields of radiation of different angular divergence into a beam where the orthogonal fields of radiation have substantially similar angular divergence (e.g., an astigmatic-free beam), or (ii) to modify radiation emitted from an electromagnetic radiation source possessing orthogonal fields of radiation of substantially similar angular divergence into a beam where the orthogonal fields of radiation have different angular divergence (e.g., an astigmatic beam).

Embodiments of the BRA beam sampler can overcome some of the prior art limitations by significantly reducing measurement errors caused by backscatter radiation impinging upon the measurement means of the beam sampler. In one embodiment, the BRA beam sampler can include a novel arrangement of refracting, reflective, and/or absorbing surfaces. The BRA beam sampler can be implemented to minimize a number of surfaces needed to measure and shape radiant energy from an electromagnetic radiation source into a working beam of known energy. The BRA beam sampler can prevent backscatter and internally reflected radiation from impinging upon the measuring means of the beam sampler which can reduce measurement errors and instability.

In one embodiment, the BRA beam sampler can include, but is not limited to, a convex optical surface, a beam splitting means, the absorptive coating, and a measurement means. The convex optical surface can receive light along a first ray path of a first medium (e.g., air, nitrogen, argon, and/or other gases) and can focus the light into a first beam within a second medium (e.g., optical glass, transparent plastic, poly methyl methacrylate (PMMA)). The beam splitting means can split incident light of the first beam into (i) a reflected beam propagating along a second ray path within the second medium, and (ii) an anamorphic-refracted beam propagating along a third ray path. The light can be split once more within the first medium and partially reflect backscattered light propagating substantially backwards along the third ray path. The measurement means can be implemented to determine an energy of the reflected beam in proportion to an energy of the anamorphic-refracted beam.

Listed hereinafter are various components, elements, and configurations that may be included with the previously mentioned BRA beam sampler. The list of components, elements, and configurations is not meant to be limiting and is not an exhaustive list.

The aforementioned BRA beam sampler can include the second medium with a refractive index greater than a refractive index of the first medium. The beam splitting means can be incorporated as a planar dielectric interface of the first medium and the second medium. The beam splitting means can be in communication with the convex optical surface and the measurement means via the second medium. The convex optical surface can receive light along the first ray path substantially perpendicular to the convex optical surface. An incident light of the first beam can impinge upon the beam splitting means within the second medium along the first ray path at an angle of incidence approximately less than a critical angle of refraction between the first medium and the second medium. In another instance, an incident light of the first beam can impinge upon the beam splitting means within the second medium along the first ray path at an angle of incidence that can be non-perpendicular to the beam splitting means.

In one instance, the anamorphic-refracted beam can propagate from the beam splitting surface along the third ray path at an angle substantially equal to 45 degrees. In another instance, the anamorphic-refracted beam can propagate from the beam splitting surface along the third ray path with an altered divergence along one axis orthogonal to the path of propagation.

The aforementioned BRA beam sampler can have the measurement means convert impinging electromagnetic energy to a measureable response by one or more methods including, but not limited to, the photoelectric effect, a photochemical response, and/or other electromagnetic or photon conversion phenomenon enabling determination of a beam energy. The measurement means can determine an energy of the anamorphic-refracted beam along the third ray path by proportional equivalency to an energy impinging upon the measurement means of the reflected beam measured as a photonic response to impinging electromagnetic radiation.

In another embodiment, the BRA beam sampler can include each of the previously listed components and can further include a convex aperture. In one instance, the convex aperture can be formed by an absence of the absorptive coating on the convex optical surface. The convex aperture can be disposed upon the convex optical surface. Typically, the convex aperture can be concentric with the first ray path through which light can be received. Typically, backscattered light propagating along the first ray path having a diameter greater than a diameter of the convex aperture can be absorbed by the absorptive coating.

In yet another embodiment, the BRA beam sampler can include each component of the previously mentioned beam sampler and can further include a field lens. The field lens can typically be disposed along the third ray path and can alter a divergence of the light through thereof propagating. In one instance, the field lens can be disposed along the ray third path at a distance substantially equal to a focal length of the field lens from an image formed by the convex optical surface and the beam splitter means. In another instance, the field lens can be disposed along the third ray path at a distance substantially coincident to an image formed by the convex optical surface and the beam splitter means. In yet another instance, the field lens can be disposed along the third ray path at a distance between one focal length of the field lens from an image formed by the convex optical surface and the beam splitter means and a distance coincident to the formed image.

In one embodiment, the BRA beam sampler can include each component of the previously mentioned beam samplers. For instance, the BRA beam sampler can include, but is not limited to, a convex optical surface, a beam splitting means, an absorptive coating, a measurement means, a field lens, and a convex aperture.

Embodiments of the present invention can be utilized with a deaerator apparatus for liquid assay as is described in U.S. provisional patent application 62/173,101 filed on Jun. 9, 2015 and having the same inventor as the present application. The deaerator apparatus provisional application is incorporated herein in its entirety.

Terminology

The terms and phrases as indicated in quotation marks (" ") in this section are intended to have the meaning ascribed to them in this Terminology section applied to them throughout this document, including in the claims, unless clearly indicated otherwise in context. Further, as applicable, the stated definitions are to apply, regardless of the word or phrase's case, to the singular and plural variations of the defined word or phrase.

The term "or" as used in this specification and the appended claims is not meant to be exclusive; rather the term is inclusive, meaning either or both.

References in the specification to "one embodiment", "an embodiment", "another embodiment, "a preferred embodiment", "an alternative embodiment", "one variation", "a variation" and similar phrases mean that a particular feature, structure, or characteristic described in connection with the embodiment or variation, is included in at least an embodiment or variation of the invention. The phrase "in one embodiment", "in one variation" or similar phrases, as used in various places in the specification, are not necessarily meant to refer to the same embodiment or the same variation.

The term "couple" or "coupled" as used in this specification and appended claims refers to an indirect or direct physical connection between the identified elements, components, or objects. Often the manner of the coupling will be related specifically to the manner in which the two coupled elements interact.

The term "directly coupled" or "coupled directly," as used in this specification and appended claims, refers to a physical connection between identified elements, components, or objects, in which no other element, component, or object resides between those identified as being directly coupled.

The term "approximately," as used in this specification and appended claims, refers to plus or minus 10% of the value given.

The term "about," as used in this specification and appended claims, refers to plus or minus 20% of the value given.

The terms "generally" and "substantially," as used in this specification and appended claims, mean mostly, or for the most part.

Directional and/or relationary terms such as, but not limited to, left, right, nadir, apex, top, bottom, vertical, horizontal, back, front and lateral are relative to each other and are dependent on the specific orientation of a applicable element or article, and are used accordingly to aid in the description of the various embodiments and are not necessarily intended to be construed as limiting.

The term "light," as used in the specification and appended claims, refers to electromagnetic radiation in the visible spectrum.

An Embodiment of a Beam Sampler

Referring to FIGS. 1-5, detailed diagrams of an embodiment 100 of a beam sampler are illustrated. Generally, the beam sampler 100 can be implemented as a backscatter reductant anamorphic (BRA) beam sampler. The BRA beam sampler 100 can be implemented to reduce a measurement error of the beam sampler due to backscatter radiation.

In one embodiment, the beam sampler 100 can include, but is not limited to, a right angle prism 102, a plano-convex lens 104, a field lens 106, a photodetector 108, and an electromagnetic radiation source 110, as shown in FIG. 1. Typically, the beam sampler 100 can include an annular convex absorptive coating 114 forming an aperture 112 on the plano-convex lens 104. Typically, the annular convex absorptive coating 114 can include, but is not limited to, single layer dielectric depositions, multi-layer dielectric depositions, metal depositions, metal-oxide depositions, various pigmented suspensions, and/or various pigmented paints.

In one example, the electromagnetic radiation source 110 can be a light emitting source including, but not limited to, a light emitting diode (LED) and a laser. It is to be appreciated that other means of emitting light can be implemented.

Generally, the plano-convex lens 104 can include the convex aperture 112 to allow electromagnetic radiation generated by the electromagnetic radiation source 110 to propagate through the plano-convex lens 104. As can be appreciated, the convex aperture 112 can be located where the annular convex absorptive coating 114 is not present. In one instance, the convex aperture 112 can be formed by the convex annular absorptive coating 114 located on a convex surface 104a of the plano-convex lens 104.

Figure 2:
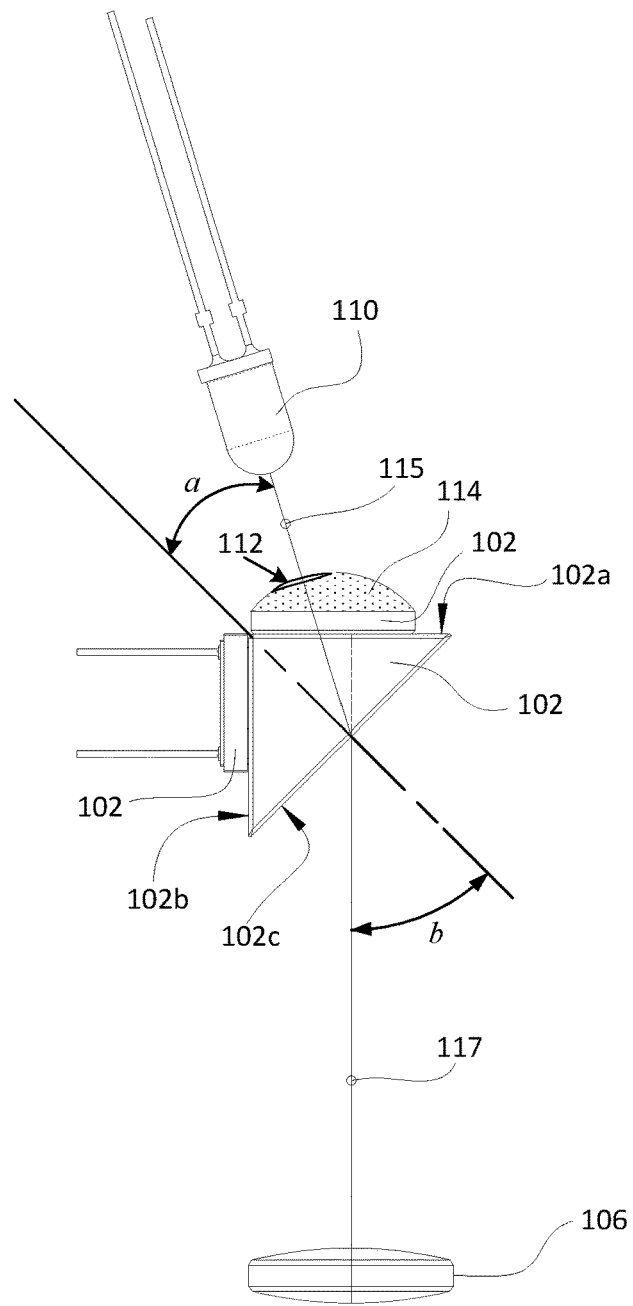
FIG. 2 is a side view of a beam sampler according to one embodiment of the present invention.
Figure 3:
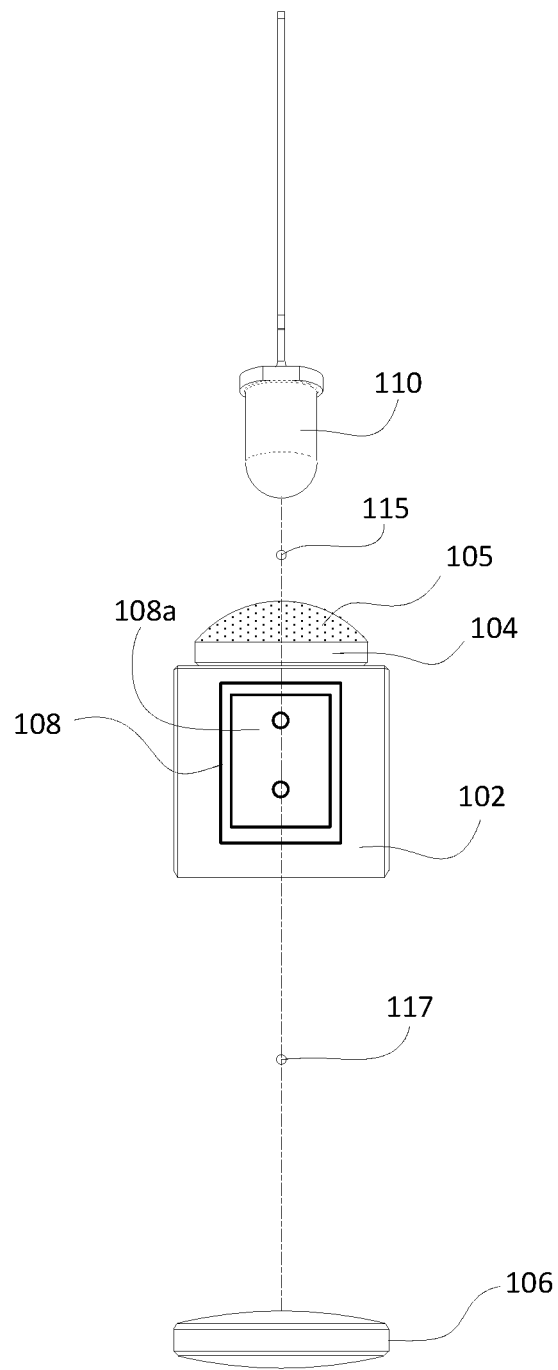
FIG. 3 is a front view of a beam sampler according to one embodiment of the present invention.

As shown generally in FIGS. 1-3, light from the LED 110 can travel along a first ray path 115 in a first medium 150 (typically air) from the LED 110 through the convex aperture 112 disposed upon the convex surface 104a of the plano-convex lens 104. The light can continue to propagate along the first ray path 115 within a second medium 160 defined by a material used to construct the plano-convex lens 104 and the right angle prism 102. The first ray path 115 can be refracted upon a transition from the second medium 160 of the right angle prism 102 to the first medium 150 along a second ray path 117. The light can continue to propagate along the second ray path 117 from the right angle prism 102 to the field lens 106 through which the light can exit the beam sampler 100.

In one embodiment, the right angle prism 102 can be a right angle triangular prism and can include a plurality of surfaces. As shown in FIG. 2, the right angle prism 102 can include a first right angle prism surface 102a, a second right angle prism surface 102b, and a third right angle prism face 102c. In one instance, the first right angle prism surface 102a can be an opposite surface, the second right angle prism surface 102b can be an adjacent surface, and the third right angle prism surface 102c can be a hypotenuse surface.

In one embodiment, a planar surface 104b of the plano-convex lens 104 can be coupled to the opposite surface 102a by an optical epoxy adhesive. For example, the optical epoxy adhesive can be epoxy no. 301-2 manufactured by Epoxy Technology, 14 Fortune Dr., Billerica, Mass. As can be appreciated, an optical epoxy adhesive that can be transparent within a wavelength in a range of interest can be implemented to couple the plano-convex lens 104 to the right angle prism 102.

The photodetector 108 can be coupled to the adjacent surface 102b by an optical epoxy adhesive to the right angle prism 102. Generally, a position of the plano-convex lens 104 on the opposite surface 102a can be determined from the second ray path 117. In one embodiment, a refracted angle b that is preferentially set to 45° from normal to the hypotenuse surface 102c can be implemented. Preferentially, the right angle prism 102 and the plano-convex lens 104 can be comprised of the same or substantially similar optical material. In one example, Schott Optical Glass no. N-BK7 can be implemented. Typically, substantially similar optical material can be implemented so that there is no change in direction of the transmitted light through the second medium 160 due to refraction. For instance, as the light propagates from the plano-convex lens 104 to the right angle prism 102, there should be little to no change in the path of the light. As can be appreciated, a direction of the first ray path 115 can be unchanged passing through the plano-convex lens 104 to the right angle prism 102.

As shown in FIG. 3, a center position of an active area 108a of the photodetector 108 can be located proximate the adjacent surface 102b.

Referring back to FIG. 2, a position of the plano-convex lens 104 on the opposite surface 102a can be further prescribed to intersect normal to the convex surface 104a of the plano-convex lens 104 along the first ray path 115. By intersecting normal to the convex surface 104a of the plano-convex lens 104, an astigmatism will not be introduced to light rays propagating into the beam sampler. The position of the plano-convex lens 104 can therefore be determinable by trigonometric relations upon a determination of angle a that is dependent on the refractive index of the right angle prism 102, a wavelength of interest, and an angle of incidence at the hypotenuse surface 102c using Snell's Law:

$$n1 \cdot \sin(a) = n2 \cdot \sin(b) \qquad 1.$$

where n2 is the refractive index of air, n1 is the refractive index of N-BK7, and b=45°. In one example, for a given wavelength of interest equal to 870 nm, the refractive index of N-BK7 at 870 nm equal to 1.5094931, and the refractive index of air equal to 1.000, the angle a would be equal to 27.933°.

Figure 4:
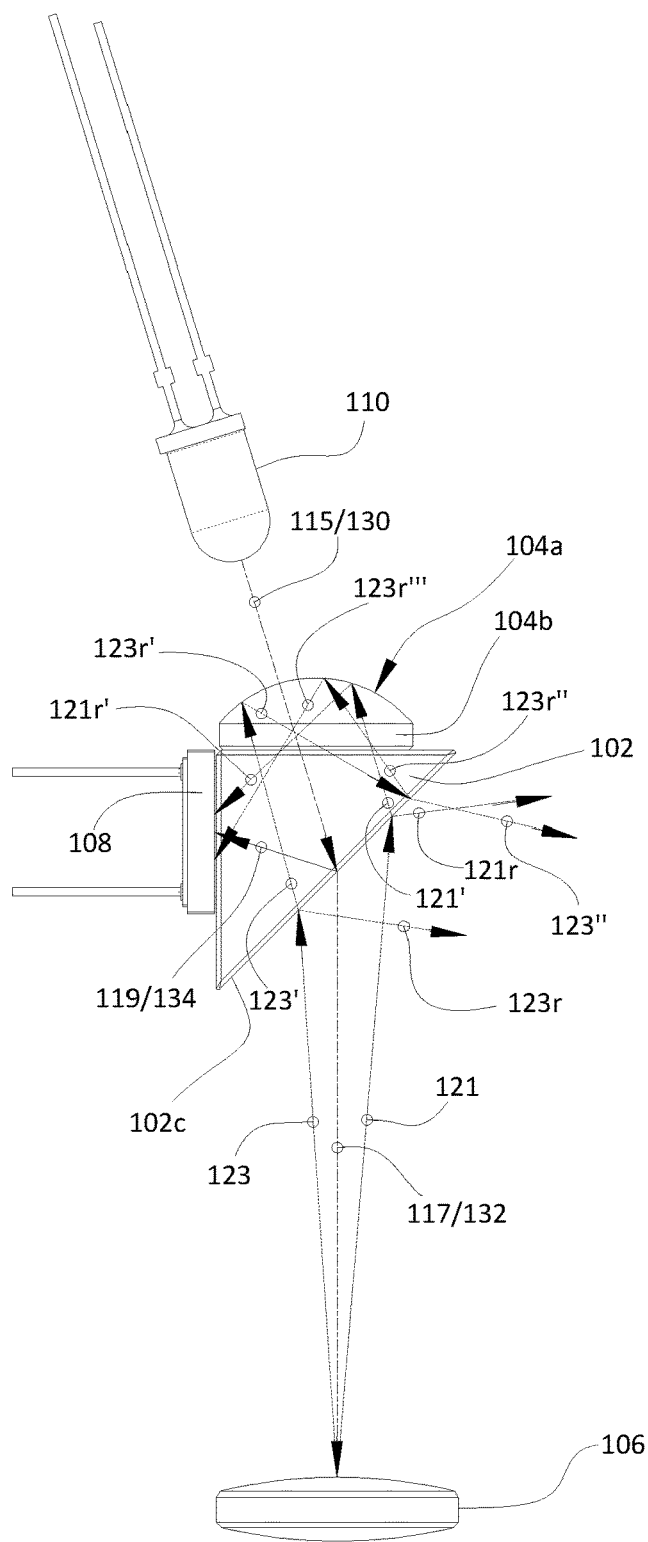
FIG. 4 is a side view of a beam sampler without a convex coating showing ray paths due to reflections according to one embodiment of the present invention.

Referring to FIG. 4, the beam sampler 100 is shown without the convex aperture 112 of the plano-convex lens 104. The plano-convex lens 104 can receive an electromagnetic radiation 130 from the electromagnetic radiation source 110 through the convex surface 104a of the plano-convex 104 lens along the first ray path 115, as generally shown in FIGS. 1-5. The convex surface 104a can focus the electromagnetic radiation (or light) 130 emitted from the electromagnetic radiation source 110 to eventually propagate to the field lens 106. The light 130 can propagate through the remainder of the plano-convex lens 104 and the right angle prism 102 as a beam without substantial change in cross-sectional area. The beam 130 can fall incident upon the hypotenuse surface 102c of the right angle prism 102 where the beam can be split into two beams of generally unequal energy. A first beam 132 can be a refracted beam which will hereinafter be referred to as the "working beam." A second beam 134 can be an internally reflected beam which will hereinafter be referred to as the "reference beam."

Typically, an energy of the working beam 132 and the reference beam 134 can be dependent on (i) the refractive indices of the dielectric materials at the refractive/reflecting interface, (ii) the angle of incidence of the incident beam, and (iii) the polarization state of the incident beam as described by the Fresnel equations of reflection, (reflection coefficients):

$$r\| = \frac{\tan(\theta i - \theta t)}{\tan(\theta i + \theta t)}. \qquad 2$$

$$r\perp = \frac{-\sin(\theta i - \theta t)}{\sin(\theta i + \theta t)}. \qquad 3$$

$$\% R = \frac{r\|^2 + r\perp^2}{2} \cdot 100\% \text{ (For un-polarized incident light.)}. \qquad 4$$

Where "r ∥" is the reflectance value for parallel polarized light, "r⊥" is the reflectance value for perpendicular polarized light, θi is the incident angle of a beam, and θt is the transmitted angle of refraction of a beam of light.

Figure 5:
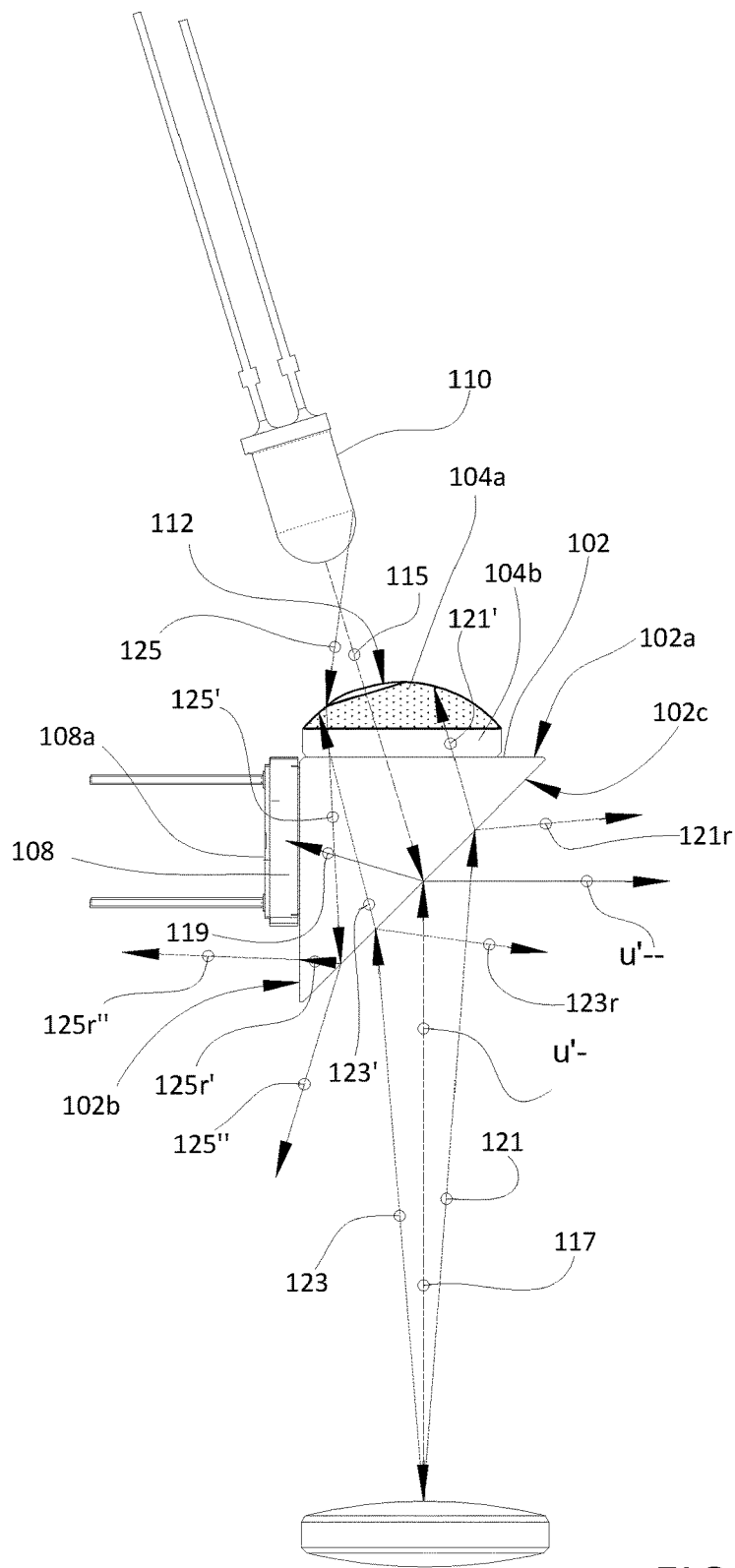
FIG. 5 is a side view showing resultant ray paths of a beam sampler according to one embodiment of the present invention.

As previously discussed, the angle of refraction can be described by Snell's law, as presented in equation 1. The angle of incidence of the beam to a beam splitter surface can be preferentially set to result in the working beam 132 propagating from the beam splitter surface (i.e., the hypotenuse surface 102c of the right angle prism) at a refracted angle of approximately 45°. The angle of incidence within the second medium 160 can typically be less than that of the critical angle of the refractive/reflective interface where a total internal reflection occurs. The angle of incidence within the second medium 160 can be greater than that of perpendicular to the beam splitter surface. As can be appreciated, the geometric configuration can favor the working beam 132 over the reference beam 134 in an amount of energy comprising each of the two beams. The geometric configuration can facilitate a rejection of a portion of backscatter radiation along a backscatter ray path u'- and u'-- from reentrance into the beam sampler 100, as shown in FIG. 5.

In one example, given a refractive/reflective interface comprised of the second medium 160 being N-BK7 and the first medium 150 being air and the beam sampler 100 operating at a wavelength of 870 nm, a percentage of light impinging upon the photodetector 108 by the reference beam 134 can be approximately equal to 5.16% for an un-polarized incident beam per equations 2, 3 and 4. The remainder of light can be transmitted as the working beam 132.

As shown in FIG. 4, the reflected reference beam 134 traveling along a third ray path 119 can intersect a center position of the photodetector 108, as shown in FIG. 4. Electromagnetic radiation impinging upon the active area 108a of the photodetector 108 can be converted to a measureable response by an electromagnetic photon conversion phenomenon including, but not limited to, photoelectric effect, photochemical response, and/or other electromagnetic or photon conversion phenomenon which can enable a determination of an energy of the reference beam 134.

In a typical implementation, an angle of incidence of the reference beam 134 to a detection means can be preferentially set so as to prevent internal reflections of the reference beam 134 from propagating along the second ray path 117 followed by the working beam 132. Alternatively, the angle of incidence can be preferentially set to prevent internal reflections of the reference beam 134 from propagating backward along the third ray path towards the hypotenuse surface 102c. For instance, an orientation of the detection means can be preferentially set at an angle other than perpendicular to the reference beam 134.

As shown in FIG. 4, light scattered backwards from the field lens 106 or beyond may do so substantially along a ray path 121 and/or a ray path 123. Backscattered radiation which is not rejected at the hypotenuse surface 102c can be refracted towards the convex surface 104a. As can be appreciated, without the annular convex absorptive coating 114 present on the convex surface 104a, a portion of the light 130 can subsequently impinge upon the photodetector 108 along a ray path 121r' and a ray path 123r'''. Light on the ray path 121r' can undergo a single internal reflection and light on the ray path 123r''' can undergo multiple internal reflections within the second medium 160. As can be appreciated, a determinable response produced by the photodetector 108 that is not a result of light reflected along the ray path 119 can be due to stray light. As such, a net response of the photodetector 108 can therefore be erroneous. For instance, the net response can be equal to a sum of an energy of the reference beam 134 plus stray light due to backscatter. As a result, the net response is greater than expected causing erroneous data.

In some embodiments, the annular convex absorptive coating 114 can be applied to the convex optical surface 104a of the plano-convex lens 104, as illustrated in FIG. 5. In embodiments including the annular convex absorptive coating 114, light that is backscattered along the ray path 121 and the ray path 123 can be refracted to the ray path 121' and 123' respectively, or they can be reflected to the ray path 121r and 123r on the hypotenuse surface 102c of the right angle prism 102. As can be appreciated, light on the refracted ray paths 121' and 123' can be absorbed by the convex absorptive coating 114 before an internal reflection occurs or the light impinges upon the photodetector 108. As a result, the amount of backscatter energy impinging upon the photodector 108 can be reduced by a factor approximately greater than 40 that which would occur if no absorptive coating were present. The absorptive coating 114 can be implemented to improve a measurement accuracy of the beam sampler 100. For instance, the beam sampler 100 can reduce a susceptibility of the beam sampler to noise modulated by the backscatter emission due to an interaction of the working beam 132 with objects and/or surfaces beyond the beam sampler 100.

Astigmatism can cause anamorphic change in a cross-section of the working beam 130 at the hypotenuse surface 102c of the prism 102 due to refraction along a length of the hypotenuse surface 102c. Astigmatism can be useful for producing a beam having a substantially circular cross-section from a radiant source emitting with two distinct orthogonal fields. For instance, a laser diode can emit a light beam with two distinct orthogonal fields. A laser diode aligned in rotation so that an emissive field possessing a greater divergence can be incident along a length of the hypotenuse surface 102c of the prism 102 can produce a working beam 132 having orthogonal fields with substantially similar divergence. The amount of astigmatism introduced into the working beam 132 can be dependent on parameters of the hypotenuse surface 102c including, but not limited to, a refractive index of the working medium, a refractive index of the prism 102, an angle of incidence, a refracted angle, and an extent of the field. As can be appreciated, judicial selection of the parameters at that hypotenuse surface 102c can result in an anamorphic change in the incident field divergence to one that can best optimize requirements of the working beam 132. For instance, the parameters can best optimize requirements of an anamorphic-refracted beam. As can be appreciated, a source radiating in orthogonal fields with the same divergence can be transformed to one of a beam possessing orthogonal fields with different divergence. For example, a beam of radiation with a circular cross-section can be transformed to a beam with an elliptical cross-section so as to pass the radiation through a slit without significant loss in energy.

Generally, the convex aperture 112 can be implemented to limit an extent of field and to obscure a direct path to the active area 108a of the photodetector 108 located on the adjacent surface 102b of the right angle prism 102.

Referring back to FIG. 5, a marginal beam of light of the electromagnetic radiation source 110 may follow a ray path 125. In one instance, light on the marginal ray path 125 may be a result of internal reflections within the electromagnetic radiation source 110 that do not contribute to an energy of the working beam 132. Since light on the marginal ray path 125 does not contribute to an energy of the working beam, the light can be considered stray light. As can be appreciated, light on the marginal ray path 125 should not be permitted to contribute to the reference beam 134. In one instance, light on the marginal ray path 125 can refract at the convex optical surface 104a of the plano-convex lens 104 at an extent of the convex aperture 112 on a ray path 125'. Light on the refracted marginal ray path 125' may exit the beam sampler 100 on a refracted ray path 125" and/or on a reflected ray path 125r' and out of the beam sampler 100 on a ray path 125r" without a contribution to the reference beam 134 along the ray path 117. As can be appreciated, the marginal beam of light can generally not contribute as an error in a signal generated by the photodetector 108.

The working beam 132 propagating from the hypotenuse surface 102c of the right angle prism 102 traveling along the second ray path 117 can travel with an angular radiation pattern determined by (i) a focal length of the convex lens 104 and the radiation source 110, and (ii) a spatial distance between the convex optical surface 104a and the radiation source 110. Typically, to limit a divergence of the beam without a loss in beam energy, the field lens 106 can be positioned along the second ray path 117 substantially at or beyond an image formed by the convex optical surface 104a of the radiation source 110. A diameter of the field lens 106 can generally be selected to include the marginal rays of the working beam 132. In one embodiment, a focal length and a position of the field lens 106 can be selected based upon a desired working beam focal ratio and a working distance of the working beam 132. As can be appreciated, for a working beam with a focal ratio greater than approximately 16, the field lens 106 can be located at distance of one focal length from the image formed by the convex optical surface 104a and the hypotenuse surface 102c.

As previously described, a specified location of the field lens 106 can be implemented to produce a working beam that can be substantially collimated. Alternately, the field lens 106 may be disposed coincident with an image formed by the convex optical surface 104a and the hypotenuse surface 102c. Typically, a focal length of the field lens 106 can be made sufficient to form an image of the convex aperture 112 at a select working distance. An alternate focal length and an alternate position of the field lens 106 can produce a beam with a substantially uniform cross-sectional intensity at a select working distance. In one embodiment, the field lens 106 may be located between one focal length from an image formed by the convex optical surface 104a and the hypotenuse surface 102c to coincidence with the image.

In one embodiment, where a divergence of the working beam 132, propagating along the second ray path 117, is sufficient for an intended use without further manipulation, the field lens 106 may be unnecessary and might otherwise be omitted if the field lens 106 is not also principal to a task of restricting a divergence of the backscattered light within the beam sampler 100 to a field that does not directly impinge upon the photodetector 108.

Alternative Embodiments and Variations

The various embodiments and variations thereof, illustrated in the accompanying Figures and/or described above, are merely exemplary and are not meant to limit the scope of the invention. It is to be appreciated that numerous other variations of the invention have been contemplated, as would be obvious to one of ordinary skill in the art, given the benefit of this disclosure. All variations of the invention that read upon appended claims are intended and contemplated to be within the scope of the invention.

I claim:
1. A beam sampler comprising:
a right angle prism, the right angle prism being defined by:
an opposite surface;
an adjacent surface; and
a hypotenuse surface;
a plano-convex lens coupled to the opposite surface of the right angle prism, the plano-convex lens including an absorptive coating;
a photodetector coupled to the adjacent surface of the right angle prism; and
an electromagnetic radiation source, wherein a beam generated by the electromagnetic radiation source passes through the plano-convex lens before falling incident upon the hypotenuse surface.
2. The beam sampler of claim 1, wherein a planar surface of the plano-convex lens is coupled to the opposite surface of the right angle prism.
3. The beam sampler of claim 1, wherein the absorptive coating is an annular convex absorptive coating located on a convex surface of the plano-convex lens.
4. The beam sampler of claim 3, wherein the annular convex absorptive coating includes an aperture.
5. The beam sampler of claim 4, wherein electromagnetic radiation generated by the electromagnetic radiation source is configured to pass through the aperture.
6. The beam sampler of claim 1, wherein the plano-convex lens and the right angle prism are manufactured from substantially similar optical material.
7. The beam sampler of claim 1, wherein the beam splits into a working beam and a reference beam after falling incident upon the hypotenuse surface.
8. The beam sampler of claim 7, wherein the working beam and the reference beam have unequal energy.
9. The beam sampler of claim 7, wherein the photodetector is configured to determine an energy of the working beam in proportion to an energy of the reference beam.
10. A backscatter reductant anamorphic beam sampler comprising:
a right angle prism including an opposite surface, an adjacent surface, and a hypotenuse surface;
a plano-convex lens coupled to the opposite surface of the right angle prism, the plano-convex lens including an annular convex absorptive coating;
a photodetector coupled to the adjacent surface of the right angle prism; and an electromagnetic radiation source, wherein a beam generated by the electromagnetic radiation source passes through the plano-convex lens before falling incident upon the hypotenuse surface.

11. The backscatter reductant anamorphic beam sampler of claim 10, wherein a portion of the plano-convex lens is free of the annular convex absorptive coating.

12. The backscatter reductant anamorphic beam sampler of claim 10, wherein the annular convex absorptive coating is applied to a convex surface of the plano-convex lens.

13. The backscatter reductant anamorphic beam sampler of claim 10, wherein the electromagnetic radiation source generates an electromagnetic radiation.

14. The backscatter reductant anamorphic beam sampler of claim 13, wherein the electromagnetic radiation propagates along a path substantially perpendicular to a convex surface of the plano-convex lens.

15. The backscatter reductant anamorphic beam sampler of claim 13, wherein the electromagnetic radiation impinges the hypotenuse surface of the right angle prism at an angle of incidence less than a critical angle of refraction between a first medium and a second medium.

16. The backscatter reductant anamorphic beam sampler of claim 15, wherein the second medium includes the plano-convex lens and the right angle prism.

17. The backscatter reductant anamorphic beam sampler of claim 15, wherein the first medium is a liquid.

18. The backscatter reductant anamorphic beam sampler of claim 13, wherein the electromagnetic radiation impinges the hypotenuse surface of the right angle prism at an angle of incidence that is non-perpendicular.

19. The backscatter reductant anamorphic beam sampler of claim 10, wherein the photodetector is adapted to determine an energy of an anamorphic-refracted beam by proportional equivalency to an energy impinging upon the photodetector by a reflected beam.

20. A beam sampler comprising:
  a right angle prism, the right angle prism being defined by:
    an opposite surface;
    an adjacent surface; and
    a hypotenuse surface;
  a plano-convex lens coupled to the opposite surface of the right angle prism;
  an annular convex absorptive coating located on a convex surface of the plano-convex lens, the annular convex absorptive coating including an aperture;
  a photodetector coupled to the adjacent surface of the right angle prism; and
  an electromagnetic radiation source.

* * * * *